(12) United States Patent
Geng

(10) Patent No.: US 7,474,932 B2
(45) Date of Patent: Jan. 6, 2009

(54) DENTAL COMPUTER-AIDED DESIGN (CAD) METHODS AND SYSTEMS

(75) Inventor: Z. Jason Geng, Rockville, MD (US)

(73) Assignee: Technest Holdings, Inc., Boston, MA (US)

( * ) Notice: Subject to any disclaimer, the term of this patent is extended or adjusted under 35 U.S.C. 154(b) by 582 days.

(21) Appl. No.: 10/973,149

(22) Filed: Oct. 25, 2004

(65) Prior Publication Data

US 2005/0089822 A1 Apr. 28, 2005

Related U.S. Application Data

(60) Provisional application No. 60/514,148, filed on Oct. 23, 2003.

(51) Int. Cl.
*G06F 19/00* (2006.01)
*A61C 13/00* (2006.01)

(52) U.S. Cl. .................................. 700/98; 433/167
(58) Field of Classification Search .............. 700/95–98, 700/117–119, 159–163, 179–185; 433/199.1, 433/201.1, 202.1, 213, 215, 218, 223, 167
See application file for complete search history.

(56) References Cited

U.S. PATENT DOCUMENTS

| | | | | |
|---|---|---|---|---|
| 5,338,198 | A * | 8/1994 | Wu et al. | 433/213 |
| 6,049,743 | A * | 4/2000 | Baba | 700/163 |
| 6,619,959 | B2 * | 9/2003 | Iiyama et al. | 433/215 |
| 6,694,212 | B1 * | 2/2004 | Kennedy | 700/163 |
| 6,832,877 | B2 * | 12/2004 | Hamada | 409/96 |
| 6,974,323 | B2 * | 12/2005 | Weigl et al. | 433/223 |
| 7,056,115 | B2 * | 6/2006 | Phan et al. | 433/24 |
| 7,077,646 | B2 * | 7/2006 | Hilliard | 433/6 |
| 7,162,321 | B2 * | 1/2007 | Luthardt et al. | 700/118 |
| 7,172,417 | B2 * | 2/2007 | Sporbert et al. | 433/24 |
| 2002/0064759 | A1 * | 5/2002 | Durbin et al. | 433/213 |
| 2002/0180760 | A1 * | 12/2002 | Rubbert et al. | 345/630 |
| 2003/0207235 | A1 * | 11/2003 | der Zel | 433/223 |
| 2003/0222366 | A1 * | 12/2003 | Stangel et al. | 264/16 |
| 2004/0085311 | A1 * | 5/2004 | Lee et al. | 345/419 |
| 2004/0175670 | A1 * | 9/2004 | Kopelman et al. | 433/24 |
| 2004/0229185 | A1 * | 11/2004 | Knopp | 433/24 |
| 2004/0245663 | A1 * | 12/2004 | MacDougald et al. | 264/16 |
| 2005/0003329 | A1 * | 1/2005 | Lehmann et al. | 433/223 |
| 2005/0069188 | A1 * | 3/2005 | Rubbert et al. | 382/128 |
| 2005/0070782 | A1 * | 3/2005 | Brodkin | 600/407 |
| 2005/0089214 | A1 * | 4/2005 | Rubbert et al. | 382/154 |
| 2006/0078842 | A1 * | 4/2006 | Sachdeva et al. | 433/24 |
| 2006/0271229 | A1 * | 11/2006 | Kopelman et al. | 700/118 |
| 2006/0275737 | A1 * | 12/2006 | Kopelman et al. | 433/213 |
| 2006/0286501 | A1 * | 12/2006 | Chishti et al. | 433/24 |

* cited by examiner

*Primary Examiner*—M. N. Von Buhr
(74) *Attorney, Agent, or Firm*—Steven L. Nichols; Rader, Fishman & Grauer PLLC

(57) ABSTRACT

The present specification describes systems and methods for interactive three-dimensional dental imaging. More specifically, the present methods and systems provide for interactive computer-aided design (CAD) in dental applications. According to one of many possible embodiments, an interactive dental computer-aided design (CAD) system includes a graphical user interface for displaying at least one three-dimensional (3D) image for viewing by an operator, an access interface for receiving input from the operator, and a prosthesis design module providing design tools for creating a virtual 3D model of a dental prosthesis responsive to operator input.

36 Claims, 5 Drawing Sheets

US 7,474,932 B2

DENTAL COMPUTER-AIDED DESIGN (CAD) METHODS AND SYSTEMS

RELATED APPLICATIONS

This application claims priority under 35 U.S.C. §119(e) to U.S. Provisional Patent Application Ser. No. 60/514,148, filed on Oct. 23, 2003 by Geng, entitled "Interactive Computer-Aided Design Software for 3D Digital Dentistry," the contents of which are hereby incorporated by reference in their entirety.

FIELD

The present methods and systems relate to three-dimensional imaging for dental applications. More specifically, the present methods and systems relate to interactive computer-aided design (CAD) for dental applications.

BACKGROUND

While a significant number of people have dental conditions that require replacement prostheses (e.g., crowns), many of these people elect not to have dental prostheses work performed because such work is traditionally costly, time consuming, and sometimes ineffective. In particular, conventional dental practice methods require that a person make at least two separate visits to a dentist for replacement prostheses work—typically a first visit for diagnosis, planning and preparation work, and a second visit for installation and fitting. The person may also be required to wear a temporary prosthesis between visits.

At the first visit, diagnostic work is performed to determine, with the patient's approval, a choice and method for treatment. In the context of a replacement prosthesis being a crown, for example, the diagnostic work often includes taking diagnostic impressions (e.g., a wax mold) of the patient's teeth for a diagnostic study of the patient's dentition. Next, the patient's tooth structure is modified in preparation to "fit" a crown. For example, the tooth that is to receive the crown is reduced in size such that the crown will "fit" on the tooth and within the patient's dentition.

A physical dental impression of the prepared tooth is taken, and a temporary crown is placed over the tooth. The dental impression is sent to a dental laboratory (usually offsite), where technicians manually design a final crown based on the dentist's prescription and the patient's physical dental impression. Typically, the final crown design is performed manually on cast stones, which is a physically labor-intensive practice that can introduce errors into the final crown. The final crown is then manufactured and sent to the dentist. With the final crown ready, the patient is recalled for the second visit, which may be scheduled days or even weeks after the first visit.

At the second visit, the temporary crown is removed, and the final crown is fitted, adjusted, and cemented into place. If for some reason the final crown does not fit properly, the patient may be required to repeat the preparation process described above and return at a later date for yet another visit. It has been found that a significant number of crowns manufactured using the above-described traditional techniques do not fit properly at the first installation, and thereby lead to repeat visits. As can be seen, traditional restoration treatment processes are long and time-consuming for both the patient and the dentist.

Traditional dental restoration procedures also suffer from additional shortcomings. For example, conventional procedures for taking physical dental impressions and designing restoration prostheses from the physical impressions are prone to distortions that can affect the final fit of restoration prostheses. These distortions can be caused by numerous factors, including technique, temperature, manual handling, technician or dentist error, patient movement, material properties and age, or salivary contamination.

Further, conventional procedures for designing restoration prostheses from physical dental impressions are labor intensive, time consuming, and costly. Prostheses are usually designed and fabricated offsite, which requires transport arrangements, costs, and time. As mentioned above, a patient may be required to wait significant amounts of time before returning to the dentist to have restoration prostheses fitted and installed. In sum, traditional dental restoration procedures are inefficient, error-prone, time consuming, labor intensive, and costly.

SUMMARY

The present specification describes systems and methods for interactive three-dimensional dental imaging. More specifically, the present methods and systems provide for interactive computer-aided design (CAD) in dental applications. According to one of many possible embodiments, an interactive dental computer-aided design (CAD) system includes a graphical user interface for displaying at least one three-dimensional (3D) image for viewing by an operator, an access interface for receiving input from the operator, and a prosthesis design module providing design tools for creating a virtual 3D model of a dental prosthesis responsive to operator input.

BRIEF DESCRIPTION OF THE DRAWINGS

The accompanying drawings illustrate various embodiments of the present methods and systems and are a part of the specification. Together with the following description, the drawings demonstrate and explain the principles of the present methods and systems. The illustrated embodiments are examples of the present methods and systems and do not limit the scope thereof.

Throughout the drawings, identical reference numbers designate similar, but not necessarily identical, elements.

DETAILED DESCRIPTION

Figure 1:
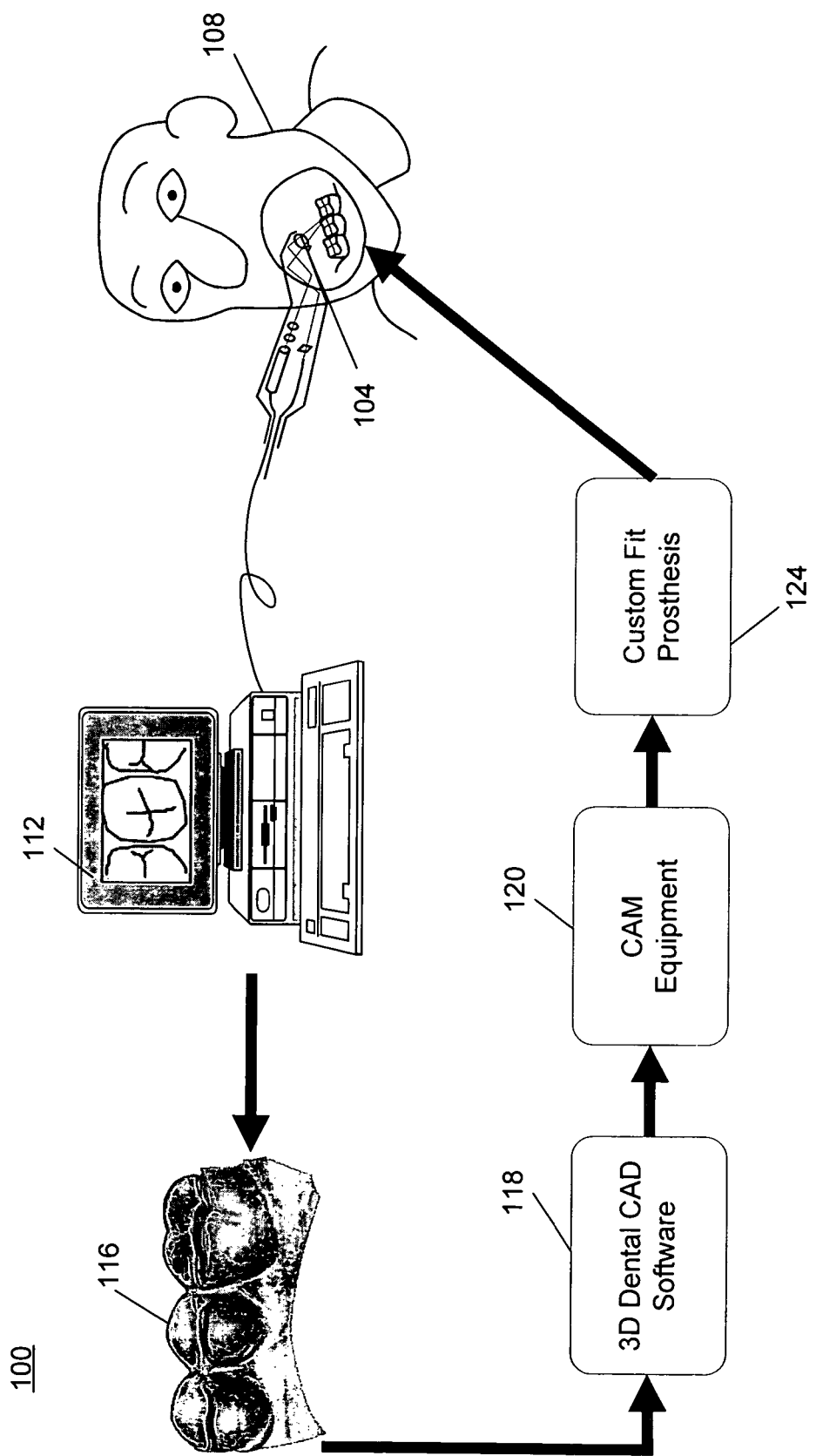
FIG. 1 is a block diagram illustrating a dental computer-aided design (CAD) system implemented in a dental prostheses treatment application, according to one embodiment.

The present specification describes systems and methods for interactive three-dimensional dental imaging. More specifically, the present methods and systems provide for interactive computer-aided design (CAD) in dental applications. The methods and systems provide operators (e.g., dentists and technicians) with comprehensive functionality for interactively manipulating three-dimensional (3D) dental image data to efficiently, accurately, and conveniently diagnose and treat dental conditions, especially conditions that require design of dental prostheses. Functions for manipulating 3D dental images include pre-processing, visualization, editing, measurement, morphing, prostheses design, virtual simulation, and other functions. These functions can be utilized by operators to design and simulate dental prostheses using interactive functions for viewing and manipulating three-dimensional digital dental images. Virtual 3D model data representative of prostheses can be outputted to other applications, including computer-aided manufacturing (CAM) equipment for manufacture of the designed restoration prostheses based on the 3D model data.

The virtual reality that is created and displayed by the present dental CAD systems and methods allows the viewer (e.g., a dentist) to move teeth and arches and/or put teeth into maximum intercuspation. The dentist can utilize the tools provided by the dental CAD systems and methods to "carve" a wax buildup by adding and subtracting "virtual wax" as needed using virtual "carving tools". Margins can be quickly determined, and the CAD systems and methods assist the dentist in visualization and design of virtual prostheses models. The ease from start to finish is a generation ahead of conventional practices because the data collected involves multiple views that are collected and added to create a 3D shape presentation or model. The provided dental CAD functions for creating and manipulating virtual 3D models eliminate the need to take, handle, store, and transport traditional physical dental impressions (e.g., wax molds) and make it possible to perform an entire dental restoration in a single patient visit, thereby improving patient comfort and costs while also increasing productivity for dental offices and laboratories.

In the following description, for purposes of explanation, numerous specific details are set forth in order to provide a thorough understanding of the present methods and systems for advanced spectrum management. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

FIG. 1 is a block diagram illustrating a dental computer-aided design (CAD) system (100) (also referred to simply as "the system (100)") implemented in a dental prostheses treatment application, according to one embodiment. As shown in FIG. 1, a camera (104) can be used to acquire image data representative of a patient's (108) dentition. The camera (104) is communicatively coupled to a computer (112) such that the acquired image data can be provided to the computer (112) for processing. The computer (112) includes predefined logic (e.g., software) configured to form a three-dimensional (3D) digital impression (116) of all or part of the patient's (108) dentition from the acquired image data. 3D dental computer-aided design (CAD) software (118) provides functionality for manipulating the 3D digital impression (116). Further, the CAD software (118) provides functionality that enables an operator to design and simulate a virtual 3D model of a dental prosthesis based on the 3D digital impression (116). As shown in FIG. 1, the 3D model can be sent to computer-aided manufacturing (CAM) equipment (120), which can manufacture custom-designed prostheses (124) based on the 3D dental model. The prostheses are then ready for installation into the patient's (108) dentition.

The camera (104) of FIG. 1 can include any sensor or sensors capable of acquiring image data representative of the patient's (108) dental dentition. The camera (104) may include charge-coupled device (CCD) cameras or sensor(s) capable of acquiring different dimensions (e.g., two-dimensional and three-dimensional views) of data representative of a dentition. The camera (104) can include an intra-oral 3D camera (104) configured to acquire 3D surface geometry data representative of the patient's (108) dentition. In one embodiment, the camera (104) includes a 3D Rainbow camera configured to acquire images using techniques described in U.S. Pat. Nos. 5,675,407, 6,028,672, and 6,147,760, the contents of which are hereby incorporated by reference in their entireties. Using the camera (104), the system (100) is configured to project a multicolored light, or rainbow projection, onto the patient's (108) tooth structure. The camera (104), in the form of a color video camera, captures the reflectance and records the position of each projected ray by color and location in the video camera. The recorded positions are recorded in digitized (numerical) form and combined together with triangulated positional software pre-calibrated for the system (100). A series of mathematical calculations produces a large data set of 3D coordinate points with (x, y, z) values. This data set may be expanded through the use of multiple projections from other perspectives as the intra-oral camera (104) is moved around the patient's (108) mouth. Using the intra-oral camera (104), an operator is able to map a target tooth, as well as adjacent and opposing teeth.

While the camera (104) can be configured to perform the preprocessing of acquired data as described above, in alternative embodiments, the computer (112) can be configured to perform preprocessing of the acquired image data. In any event, the computer (112) is configured to receive and further process the image data acquired by the camera (104).

The computer (112) provides for the execution of processing steps by which the acquired image data can be manipulated, either automatically or in response to operator commands. The computer (112) can include any device or combination of devices that allows the processing of the system (100) to be performed. The computer (112) may be a general purpose computer capable of running a wide variety of different software applications or a specialized device limited to particular functions. In some embodiments, the computer (112) is a network or other configuration of computing devices. The computer (112) may include any type, number, form, or configuration of processors, system memory, computer-readable mediums, peripheral devices, and operating systems. In one embodiment, the computer (112) includes a personal computer (PC), which may be in the form of a desktop, laptop, pocket PC, personal digital assistant (PDA), tablet PC, or other known forms of personal computers.

The computer (112) includes at least one access device and/or interface that allow the operator to utilize the functionality of the computer (112). The access device and/or interface can include but is not limited to a keyboard, mouse, touch screen, stylus, joystick, light pen, trackball, voice interactive function, three-dimensional glove, solid three-dimensional mouse ball, graphical user interface (GUI), display screen, printer, and other known input or output devices and interfaces. Through these interfaces and access devices, the operator can manipulate and otherwise direct processing of the 3D digital impression (116) and 3D virtual models as will be described in detail below.

The functionality of the system (100) can be embodied or otherwise carried on a medium or carrier that can be read by the computer (112). The medium carrying instructions (e.g., software processes) for the computer (112) can be part of or otherwise communicatively coupled to the computer (112). Program(s) of the computer-readable carrier define functions of embodiments and can be contained on a variety of signal-bearing media, which include, but are in no way limited to, information permanently stored on non-writable storage media (e.g., read-only memory devices within a computer such as CD-ROM or DVD-ROM disks readable by a CD-ROM drive or a DVD drive); alterable information stored on writable storage media (e.g., floppy disks within a diskette drive or hard-disk drive or read/writable CD or read/writable DVD); or information conveyed to a computer by a communications medium, such as through a computer or telephone network, including wireless communications. The latter embodiment specifically includes information downloaded from the Internet and other networks. Such signal-bearing media or computer readable carriers, when carrying computer-readable instructions that direct functions of the present systems and methods, represent embodiments of the present systems and methods.

The computer (112) is capable of executing processes for manipulating and otherwise processing the acquired image data for dental applications. In one embodiment, the computer (112) is capable of fanning the 3D digital impression (116) from the acquired image data in accordance with instructions provided by software running on the computer (112). Known techniques for merging or overlaying images can be implemented to form the 3D digital impression (116) from acquired images of the patient's dentition. In one embodiment, the 3D digital impression (116) is formed from the acquired image data using techniques disclosed in U.S. Patent Applications filed concurrently with this application by Geng, the first having application Ser. No 10/973,533 and and entitled "A System and a Method for Three-Dimensional Imaging Systems," now pending, and the second having application Ser. No. 10/973,853 and and entitled "Method and Apparatus for Three-Dimensional Modeling via an Image Mosaic System," now pending, the contents of which are hereby incorporated by reference in their entireties.

As shown in FIG. 1, the 3D digital impression (116) can be provided to the 3D dental CAD software (118). The dental CAD software (118) can be implemented to run on the computer (112). The dental CAD software (118) is capable of receiving interactive operator instructions and manipulating the 3D digital impression (116) based on the received instructions and then presenting the updated image for viewing by the operator. In addition to functions for manipulating 3D dental images, the dental CAD software (118) provides computer-aided design functions for creating virtual 3D models of prostheses. The interactive dental CAD functions provided by the system (100) will be described in detail below.

The 3D model data can be provided to the CAM equipment (120) shown in FIG. 1. The CAM equipment (120) can use the 3D digital model as a guide for fabrication of the prostheses (124). The fabrication may be automatic or responsive to operator input. Known fabrication techniques can be used or modified to utilize the 3D model data as a guide for prostheses fabrication.

It should be noted that the system (100) of FIG. 1 is versatile in that it is capable of providing many fabrication options with many materials and techniques. A wide variety of known fabrication techniques for various prostheses (124) can be used to manufacture the prostheses (124) based on the 3D model data generated by the system (100). The prostheses (124) can include a wide range of dental devices, including but not limited to crowns, implants, inlays, caps, retainers, dentures, sealants, bridges, and other known dental devices.

The fabricated prostheses (124) is ready for installation into the patient's (108) dentition using techniques and procedures known to those skilled in the art.

While an exemplary implementation of the system (100) is shown in FIG. 1, those skilled in the art will recognize that the exemplary components illustrated in the Figure are not intended to limit the present invention. Indeed, those skilled in the art will recognize that other alternative hardware environments may be used without departing from the scope of the present invention. Further, the present dental imaging systems and methods are not limited to dental restoration procedures and applications.

Figure 2:
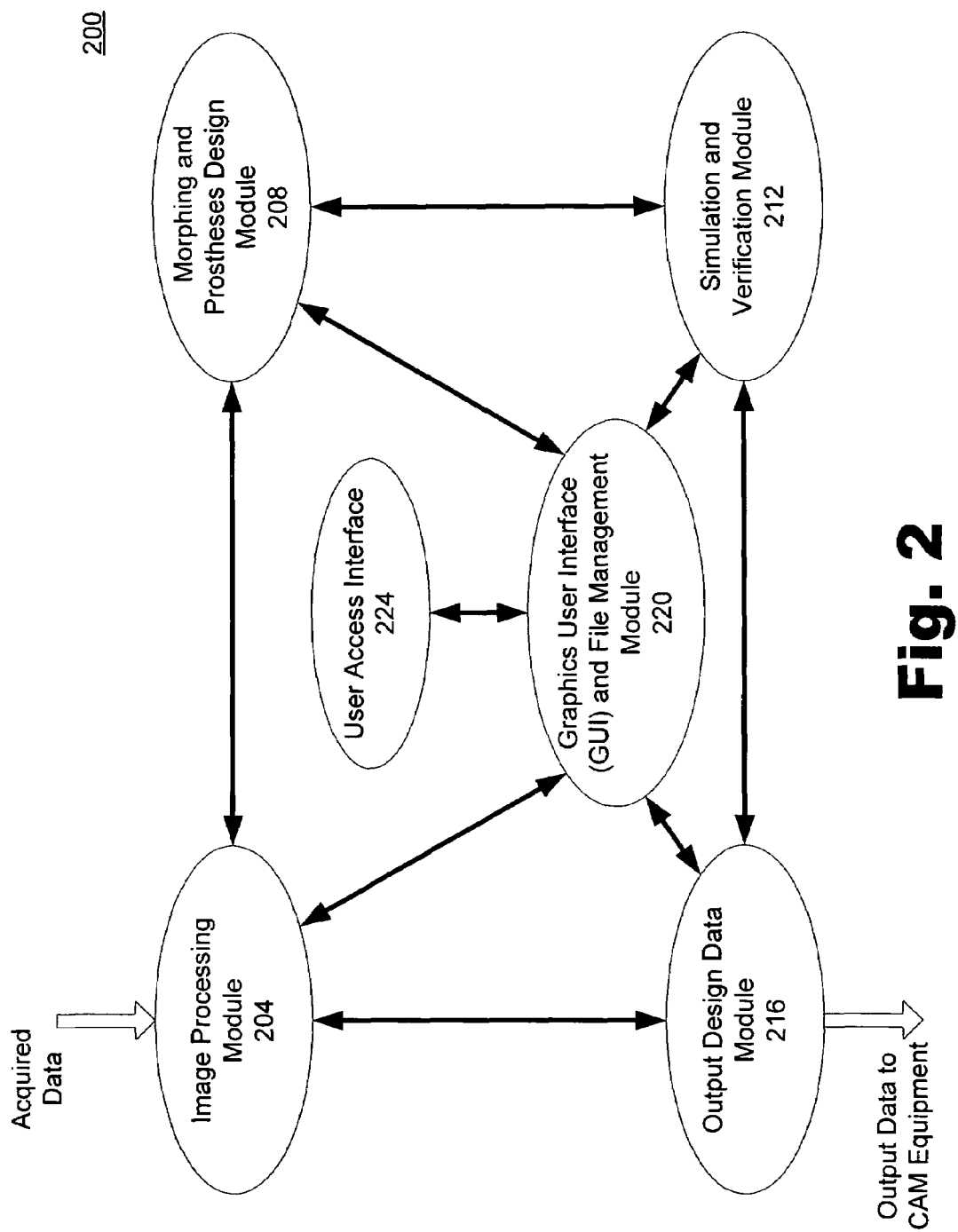
FIG. 2 is a block diagram illustrating a software architecture framework for the dental imaging system of FIG. 1, according to one embodiment.

FIG. 2 is a block diagram illustrating a software architectural framework for the dental CAD system (100) of FIG. 1, according to one embodiment. As shown in FIG. 2, the framework can include an image processing module (204), a morphing and prostheses design module (208), a simulation and verification module (212), and an output data design module (216), all capable of communicating with each other. The modules (204, 208, 212, and 216) are also able to communicate with a graphical user interface (GUI) and file management module (220), which is in communication with a user access interface (224).

The GUI and file management module (220) and user access interface (224) provide operators with interactive tools and views for manipulating 3D images using the framework (200). 3D images are presented to operators by way of graphical user interface windows that can handle 3D image visualization and manipulation functions. As discussed above, the GUIs can be presented to operators using a screen of the computer (112). The user interface module (224) is configured to interact with any of the access devices listed above to receive and process operator input. 3D image editing functions are also incorporated into the user interface module (224) to provide both a diagnostic tool and a communication tool for communicating information to dentists, patients, and lab technicians. This allows dentists to visually demonstrate diagnoses and prescription orders to patients and lab technicians.

The GUI and file management module (220) also provides functionality for managing the storage and retrieval of 3D images. The module (220) can interface with one or more databases in which files representing the 3D images can be stored and accessed.

In the embodiment shown in FIG. 1, interactive CAD functions are provided by the image processing module (204), morphing and prostheses design module (208), simulation and verification module (212), and output data design module (216) for interactively manipulating 3D images. These modules (204, 208, 212, 216) will now be described in more detail.

The image processing module (204) is configured to perform 3D image editing functions and enable operators to modify 3D image data interactively and conveniently. The image processing module (204) includes various image-filtering functions, including functions for smoothing images or reducing/eliminating the noise in the images. The functions provided by the image processing module (204) can be applied to an entire 3D image data set or to selected local areas of an image. The image processing module (204) can include a number of sub-modules configured to perform various editing and other image processing functions.

Figure 3:
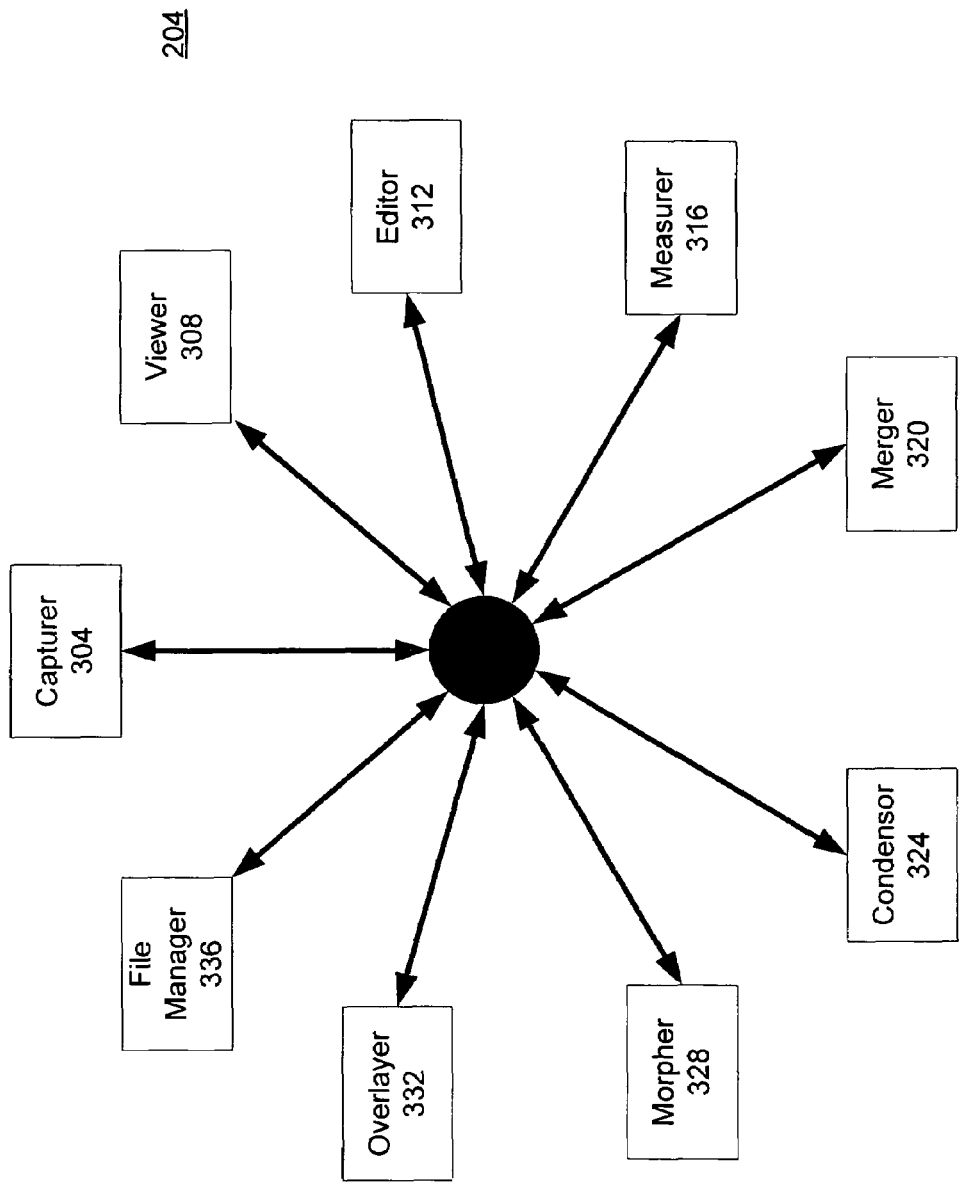
FIG. 3 is a block diagram illustrating the image processing module of FIG. 2, according to one embodiment.

FIG. 3 is a block diagram illustrating sub-modules that provide functionalities of the image processing module (204) of FIG. 2, according to one embodiment. As shown in FIG. 3, the sub-modules can include a capturer (304), viewer (308), editor (312), measurer (316), condenser (320), morpher (324), overlayer (328), and file manager (332), all in communication with one another.

The capturer (304) controls processes for acquiring image data from the camera (104; FIG. 1). The capturer (304) may include software drivers for acquiring images using various types of cameras (104; FIG. 1), including both analog and digital formats. The capturer (304) is able to handle data from both monochromic and color image sensors. Further, both 2D and 3D image data can be acquired by the capturer (304).

The viewer (308) can include general-purpose visualization software for viewing and manipulating 3D impressions and models. The software provides functions for manipulating 3D objects onscreen, including functions for rotation around and translation along three spatial axes to provide full six degrees of freedom (DOF) manipulation capabilities. Additional manipulation functions include zooming in/out, automatic centering, and scaling a displayed 3D object to fit the screen size. The viewer (308) can also be configured to display 3D objects at multiple resolutions during the manipulation in order to improve the speed of operation. The viewer (308) further provides multiple viewing windows that are controllable by operators for simultaneously viewing 3D objects from different perspectives. Multiple rendering modes are also provided, including surface, point of cloud, mesh, smoothed surface, and transparency modes. Rendering results may be optimized by setting material properties, display, color, and other related settings. In addition, the viewer (308) can be configured to recognize short-cut keys for specific functions, especially frequently-used functions. The viewer (304) also provides access to online documentation. It is further contemplated that the viewer (308) can be configured to provide many known functions for interactive manipulation of 3D images so that operators are able to conveniently and intuitively view 3D objects for purposes of study and/or manipulation.

The editor (312) can include general-purpose 3D model editing software that allows operators to modify 3D data files interactively and conveniently. The editor (312) allows operators to modify and/or eliminate any undesirable area(s) on the original 3D image obtained from the camera (104; FIG. 1), remove abnormal data point(s), and clean up the acquired image data to reduce the sizes of image data files. 3D objects can be edited, including triangular regions, vertices, local areas, and an entire data set. Known editing functions can be employed, including typical editing functions that provide for deleting, creating, and modifying objects. The editor (312) can also provide various filtering functions (e.g., smoothing and noise removal) that can be applied to entire 3D data sets or to selected local areas.

The measurer (316) provides measurement tools that enable direct extraction of various 3D parameters from a 3D model. Measurement parameters can include (x, y, z) coordinates of a feature point, 3D distance between points, surface distance between points, area, and 3D volume.

The merger (320) provides tools that enable operators to integrate multiple uncalibrated 3D images into a single 3D digital impression (116; FIG. 1). A manual mode requires operators to specify corresponding points among multiple 3D images. The merger (320) is able to bring the 3D images together and optimize the geometric registration of these images. An "auto" mode provides intelligent capability that searches the common points among multiple images based on their geometric features, such as curvatures. From the identified common points, the acquired set of multiple 3D images can be merged automatically. Alternatively, image registration techniques known to those skilled in the art can be used to merge the acquired images together to form the 3D digital impression (116; FIG. 1).

The condenser (324) provides tools for compressing 3D image data based on 3D geometric features, which can dramatically reduce the size of 3D image files while preserving essential features.

The morpher (328) provides morphing tools that enable operators to alter the 3D data in an interactive fashion. In particular, the 3D digital impression (116; FIG. 1) can be morphed using known image editing techniques applied to dental imaging. The 3D digital impression (116; FIG. 1) can be morphed by the operator to prepare it for use as a baseline to guide creation of a virtual 3D model of restoration prosthesis. 3D models can be created and morphed using the morpher (328), including model designs of dental prostheses.

The overlayer (332) provides tools for accurate registration between 3D images and 2D images acquired by the camera (104; FIG. 1). The resolution of acquired 2D and 3D images can differ significantly. The overlayer (332) provides algorithms that can determine the image with lower resolution and overlay it onto the image with higher resolution.

The file manager (336) provides various file format capabilities for exporting image data, including Stereolithography (STL) data format), Points of Cloud (PNT), Raw (Data Matrices), and other known or proprietary formats.

Returning now to FIG. 2, the morphing and design prostheses design module (208) provides interactive computer-assisted design and simulation tools that enable operators to define margins from 3D images and to modify 3D surface data in a "free-form" fashion to generate desired prosthesis design. The morphing functions assist operators in the design of dental prostheses in a virtual 3D space. Further, the module (208) provides functions for predicting postoperative anatomy without cumbersome manual intervention. By utilizing the functions of the morphing and prostheses design module (208), operators are able to produce highly accurate computer-aided virtual designs of prostheses (124; FIG. 1).

The simulation and verification module (212) performs 3D simulations to identify and verify interference of the designed prostheses with its neighboring and opposite teeth. Such simulation involves coordinating multiple 3D objects. Typical geometric parameters will be measured or extracted, including but not limited to (x, y, z) coordinates of surface points, 3D distances, curvature surface distances between two points, surface areas, 3D volumes, pre-op and post-op comparisons, etc. By utilizing the functions of the simulation and verification module (212), operators are able to verify accuracy and workability of prostheses designs using a virtual 3D space.

The output data design module (216) provides functionality for forming and outputting a completed digital design of a dental prosthesis, e.g., the virtual 3D model. The output can be in various standard and proprietary data formats, such as stereolithography (STL) for rapid prototyping, initial graphics exchange specification (IGES) for CAM Tool Path Generation, PNT (Points of Cloud), Raw (Data Matrices), and other known formats.

As shown in FIG. 2, the output data can be provided to the CAM equipment (120; FIG. 1). As discussed above, the CAM equipment (120; FIG. 1) is configured to receive the output data in a suitable format and fabricate prostheses based on the 3D model represented by the output data.

Given the functions provided by the framework (200) shown in FIG. 2, operators are able to utilize interactive 3D imaging functions for various aspects of dental care. Interactive 3D imaging may be used to enhance dental examination procedures and related record keeping. In particular, interactive 3D imaging functionality can be used to enhance restorative care procedures and results. In addition to enabling design of virtual dental restoration prostheses, 3D imaging can provide support for automated clinical practice guidelines and quality assurance procedures, as well as support other clinical phases of restorative care including examination, diagnosis, treatment planning, and treatment. The following discussion describes different roles of 3D imaging in various aspects of the restorative care spectrum.

Figure 4:
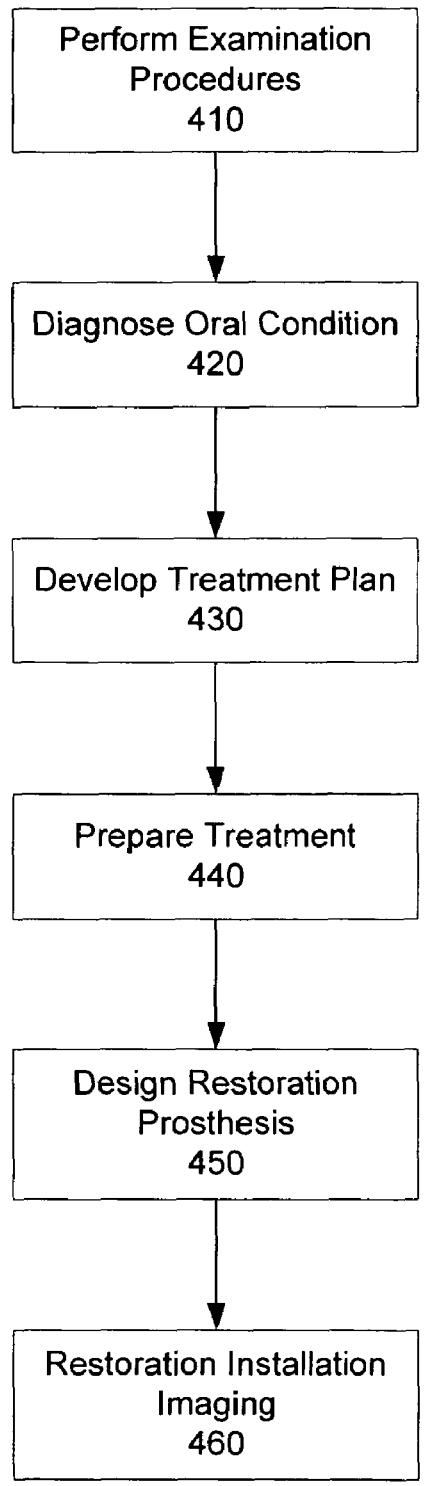
FIG. 4 is a flowchart diagram illustrating steps of a restorative care method that utilizes interactive 3D imaging, according to one embodiment.

FIG. 4 is a flowchart diagram illustrating steps of a restorative care method that utilizes interactive 3D imaging, according to one embodiment. At step (410), examination procedures are performed using interactive 3D imaging functions provided by the dental CAD system (100; FIG. 1). 3D intra-oral images are valuable adjuncts to routine clinical examinations in that they combine 3D data with color photographic data of intra-oral structures. This combination of data introduces a new and unique examination process, which elevates the existing patient record documentation baseline provided by conventional dental charting, radiographs, and photographs. This information can be used to facilitate automated dental charting as the 3D image identifies a restoration as a whole entity from a virtually unlimited number of angles as opposed to a 2D image, which can only interpret the image in one plane. Additionally, 3D dental images can be used as a more accurate legal record of pre-existing conditions and treatment rendered as volumetric changes to oral structures can be assessed and visualized. Dentists and technicians can view 3D images of a patient's (108; FIG. 1) dentition from multiple views and resolutions as part of routine clinical examinations. Records in the form of 3D images can be archived in volumetric databases. 3D dental images will also add an extra dimension of information for forensic identification purposes and will provide detailed information for etiological and epidemiological studies.

At step (420), the dental CAD system (100; FIG. 1) is used to diagnose oral conditions. 3D data imaging and mapping of dental structures has numerous applications in the area of dental diagnosis. A fundamental value is an ability to make detailed volumetric comparisons of dental structures either chronologically within the same patient (108; FIG. 1) or to compare the patient's (108; FIG. 1) dentition to a reference table normalized to that patient's (108; FIG. 1) demographics. In either case, the system (100; FIG. 1) can indicate specific areas in the dentition where structure loss or change has occurred and focus the provider's attention on those changes. This provides what can be referred to as differential diagnoses. Further, the system (100; FIG. 1) can be configured to provide a list of different diagnoses consistent with the identified changes to dental structure. A few examples of how 3D imaging can support oral diagnoses will now be discussed.

As "normal" 3D dental data is accumulated through routine examinations or through large-scale studies, average value lookup tables can be generated for various demographic groups. Average value data of craniofacial skeletal landmarks have been used for years as the basis for orthodontic treatment to correct malocclusions and to guide a patient's growth and development. 3D imaging can supplement 2D lateral cephalograms to accurately record existing 3D relationships between dentition landmarks and to track changes in their positions as treatment progresses.

Changes in oral structures due to attrition, erosion, or abrasion can be diagnosed with the assistance of 3D imaging provided by the system (100; FIG. 1). A comparison of the patient's (108; FIG. 1) 3D hard tissue profile to anatomic norms, as mentioned in the previous paragraph, would highlight areas where excessive structure loss has occurred. Applications incorporating oral pathology business rules will assist the provider in making a selection from a hierarchical list of differential diagnoses. For instance, excessive structure loss from the lingual surfaces of the maxillary anterior teeth in a young adult female would suggest a possible diagnosis of bulimia. Another example includes identification of "V-shaped" notches on the buccal surfaces of posterior teeth, which notches suggest toothbrush abrasion.

Diagnoses are not limited to static conditions as in the examples listed above. The ability to image both dental arches in 3D and to then record the centric and eccentric working relationships between them allows detailed analysis of occlusal function and dysfunction that was previously available only after lengthy conventional procedures involving making impressions, pouring diagnostic casts, and completing a diagnostic mounting. The occlusal analysis component of the system (100; FIG. 1) can indicate interferences in the occlusal contacts between the two arches in either the static maximum intercuspation or centric occlusion position or in dynamic eccentric positions depending on a selected or predefined occlusal profile.

Once appropriate diagnostic procedures have been performed, a treatment plan can be developed that reflects the needs of the oral condition, the capabilities of the dental treatment team, and the desires of the patient (108; FIG. 1). Different combinations of known manual procedures and the imaging capabilities provided by the system (100; FIG. 1) can be utilized to develop an appropriate treatment plan at step (430) of FIG. 4. For example, a conventional manual diagnostic wax-up can be performed to determine the 3D contours and occlusion for the proposed treatment. The wax-up incorporates the totality of treatment modalities and may include occlusal adjustment, esthetic re-contouring, single unit restorations, fixed partial dentures, removable partial dentures, implants, extractions, and tooth movement. 3D imaging can be used to enhance the development of a proposed treatment plan by supplementing current procedures or eliminating the manual procedures entirely.

The following alternatives involve the use of diagnostic casts, diagnostic wax-up and 3D imaging in various combinations. In one embodiment, a diagnostic wax-up can be accomplished and then imaged to provide a 3D data baseline of the final contours and occlusion of the proposed treatment. In another embodiment, a 3D image scan of diagnostic casts can be performed and then the digital images would be processed to reflect procedures to be accomplished during proposed treatment. In yet another embodiment, a preoperative 3D image scan of oral tissues during the diagnosis and treatment planning phase can take the place of diagnostic casts. Digital images would be processed in a similar manner as above to reflect procedures to be accomplished during proposed treatment. In all three of these embodiments, final 3D data profiles of proposed treatments can be used throughout treatment to provide a digital operative template for procedures to be accomplished, as well as to provide a status of the progress of treatment.

Figure 5:
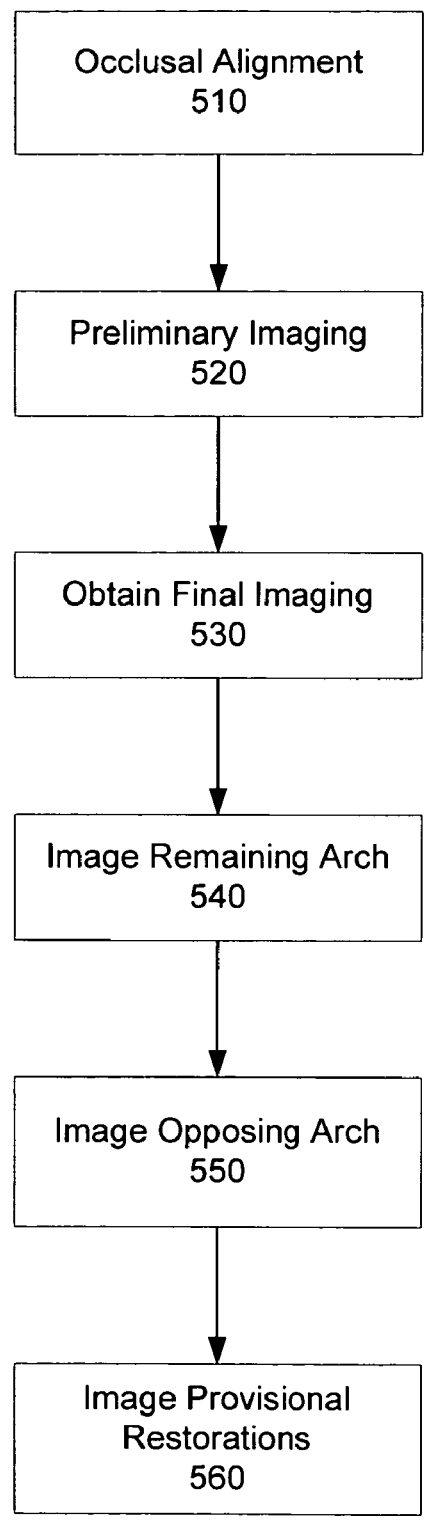
FIG. 5 is a flowchart diagram illustrating steps of dental restoration treatment preparations that utilize interactive 3D imaging, according to one embodiment.

The contributions of 3D imaging to restorative dental treatments provide significant benefits in the clinical treatment phase that is performed at step (440) of FIG. 4. With the use of 3D imaging functions provided by the system (100; FIG. 1), dentists will realize significant time and cost savings in their clinical treatment. Dentists can also incorporate true clinical quality assurance guidelines and feedback into their practice. The following steps, which are shown in FIG. 5, detail clinical procedures that can be implemented at the preparation appointment by utilizing the interactive 3D imaging functions provided by the system (100; FIG. 1).

At step (510) of FIG. 5, occlusal adjustments are performed. Occlusal adjustments are often an adjunctive treatment to restorative procedures and are generally performed prior to tooth preparation. An occlusal adjustment is an irreversible clinical procedure, which should be well planned prior to its performance. The 3D data impression (116; FIG. 1) of the dentition that has the planned occlusal adjustment incorporated is an ideal roadmap to assist a clinician in the actual intra-oral procedures for occlusal adjustments. As full mouth occlusal adjustment can be a complex treatment, the 3D imaging modality provided by the system (100; FIG. 1) enables the clinician to re-image as necessary to check treatment progress.

At step (520) of FIG. 5, preliminary imaging of prepared teeth is utilized for treatment preparation. The type of restoration for any individual tooth or group of teeth should be indicated in the treatment plan. This information can be made available to the 3D morphing and prostheses design module (208; FIG. 2) via an interface to a dental practice management application. The standard recommended preparation guidelines for that type of restoration can be stored in the design module (208; FIG. 2) and used as a basis for comparison to the actual preparation. Thus, preliminary imaging of prepared teeth can be utilized for comparison with a predetermined baseline. The comparison can then be used by dentists to check certain factors that can help identify any potential issues that may affect the restoration process. For example, 3D imaging can be used to check alignment, margin design, tooth reduction, and retention and resistance form.

With respect to alignment, the axial surfaces of the preparations must all be convergent in order for a single restoration, splint, or fixed partial denture to be inserted. A 3D image scan can be used to analyze the axial surfaces and verify convergence. This analysis can evaluate abutment alignment (path of draw), undercuts on individual preparation(s), and/or undercut between preparation(s) and adjacent teeth.

With respect to margin design, in order for there to be a smooth, healthy, cleansable, and esthetic transition between the restoration and the natural tooth, the margin must be designed and prepared properly. 3D imaging can provide for evaluation of margin design for an indicated restoration, placement of the margin on specific areas of tooth, placement of the margin relative to gingival tissues, and/or placement of the margin relative to a cementoenamel junction.

With respect to tooth reduction, the proper amount of tooth reduction should be performed to maintain proper anatomic and esthetic contours. Sufficient tooth reduction should be performed in order to provide sufficient bulk of restorative material to ensure restoration strength and rigidity. Additional tooth reduction is usually necessary in cases where esthetic veneers will be used. Interactive 3D imaging provides for evaluation of tooth reduction criteria, including but not limited to axial reduction (e.g., buccal/lingual and mesial/distal) and/or occlusal/incisal reduction.

With respect to the checking of retention and resistance form, preparations should exhibit certain key criteria in order for the restoration to be retained on the supporting structures. These retention and resistance form criteria can be assessed by the 3D imaging system (100; FIG. 1) as part of preliminary imaging processes. These criteria can include but are not limited to axial wall angulation, axial wall length, line angle contours, and sufficient remaining tooth structure.

Once the preliminary imaging analysis has been completed, a final 3D image (e.g., the 3D digital impression (116; FIG. 1)) of the prepared teeth may be obtained at step (530) of FIG. 5. This image provides the final image data upon which the restorations will be designed. To help ensure the accuracy of the final 3D image, the system (100; FIG. 1) can implement evaluations steps, which can include but are not limited to confirming correction of any problems found in preliminary imaging, identifying and correcting any artifact data, and verifying and indicating margins.

If desired, the remainder of the arch containing the preparations may be imaged by the system (100; FIG. 1) at step (540) of FIG. 5. This provides valuable data for the contralateral teeth if those teeth are present and in good condition. Full arch images are necessary for some types of restorations, e.g., if full arch occlusion is to be used.

3D imaging of the opposing arch segment opposite the preparations can also be obtained at step (550) of FIG. 5 to provide data for the occlusal part of the fabrication process. Imaging of the entire opposing arch is necessary for some types of restorations, e.g., when full arch occlusion is required.

At step (560) of FIG. 5, provisional restoration imaging functions can be performed. Even if restorations can be fabricated in a short period of time using the system (100; FIG. 1), there are still numerous uses for provisional restorations for treating certain oral conditions. Provisional restorations can be used when soft tissue healing is required prior to final imaging, or to determine the appropriate spatial relationships of teeth, particularly when multiple teeth or excessive supporting tissues are missing. Provisional restorations are also useful in developing esthetic profiles that will be used in the final restoration. Factors influencing the esthetics of provisional restorations such as lip lines, smile line, lip support, anterior tooth overjet and overbite, axial contours, incisal edge shape and contour, tooth length, etc. can be worked out and altered in the provisional restoration. Once the form of the provisional restoration is finalized it can be imaged to provide a reference (e.g., the virtual 3D model) for the fabrication of the final restoration.

Returning now to FIG. 4, restoration prostheses can be designed at step (450) using interactive 3D imaging functions provided by the system (100; FIG. 1). The prostheses fabrication phase can consist of two parts, a preparation phase and a fabrication phase. Combined, these phases will culminate in the creation of a final 3D data set (e.g., the 3D digital model) that can be used to directly fabricate the restoration. Once the final image of the prepared teeth is obtained as discussed above, the final image should be put in the context of the environment in which the restorations will be fabricated. For simple cases, the prepared tooth, its adjacent teeth, and the opposing tooth data may be all that is acquired for the fabrication process. For complex cases, the restoration(s) may be fabricated in the context of the whole arch or mouth environment. The level of environmental contextualizing depends on the type and nature of an oral condition. The 3D imaging functions provided by the system (100; FIG. 1) can help dentists determine what level of context should be considered.

At the individual tooth level, the system (100; FIG. 1) enables evaluation of the removal of artifacts and the amount and location of die spacer. At the single arch level, evaluation can include analysis of contralateral teeth, arch occlusal plance profile, and arch width. In the context of the entire mouth level, 3D images can be used to evaluate tooth-to-tooth occlusal relationships, centric occlusal contacts, eccentric contacts, anterior guidance mechanisms, and orthodontic arch relationships.

Once context has been determined and analyzed in the preparation phase, the system (100; FIG. 1) can be utilized for the fabrication phase. In this phase, operators are able to utilize a number of fabrication tools provided by the system (100; FIG. 1). In particular, the morphing and prostheses design module (208; FIG. 2) provides an extensive toolset that enables operators to properly and accurately design different types of virtual prostheses. In the context of an entire mouth environment, the toolset can be configured to provide functions for selecting an occlusal scheme for the whole mouth if the scheme is not specified as part of diagnostic assessment. The toolset can be further configured to provide functionality for determining the occlusal plane level, the anterior/posterior occlusal plane curvature, the mediolateral occlusal plane curvature, the centric occlusal contact scheme, and the disclusion mechanics. These criteria can then be used to guide the design of virtual restoration prostheses.

At an individual tooth level, the morphing and prostheses design module (208; FIG. 2) provides tools helpful for designing virtual prostheses. These tools can include but are not limited to an occlusal tool, proximal tool, gingival tool, pontics tool, framework design tool, carving tools, digital "wax" builder, and output device tool, which will now be described in more detail.

The occlusal tool enables an operator to select an occlusal scheme if not already selected for the whole mouth. Occlusal rests can be selected if necessary for a particular restoration (e.g., removable partial dentures). Centric and eccentric occlusal contacts and occlusal table width can be verified and modified using the occlusal tool. The occlusal tool may also provide for determining cusp angles from intact contralateral teeth, which can be determined functionally or by exact angles specified. An option for selecting the mirror image of the contralateral tooth can also be provided. The occlusal tool can further provide for verifying and modifying the number of cusps for molars and premolars, as well as the height and width of proximal margins. The system (100; FIG. 1) can be configured to calculate an appropriate occlusal domain to serve as a design envelope beyond which designed prosthesis should not extend. A dynamic domain can also be calculated based on interference constraints associated with possible conflicts caused by motion of upper and lower jaws.

The proximal tool enables operators to select and modify the curvature shape for proximals, which is generally a smooth convex shape from the occlusal table to the gingival. The proximal tool can further provide for incorporating proximal box or space for precision attachment(s) and for shaping proximal contours for certain restorations (e.g., removable partial denture clasp arms, guide planes, or major/minor connectors). With the proximal tool, operators are able to verify and modify the height and width of proximal contact(s). An option for selecting the mirror image of a contralateral tooth may also be provided.

The gingival tool enables operators to select and modify a type of margin and an emergence angle. The gingival tool can also be equipped with an option for selecting the mirror image of a contralateral tooth.

The pontics tool enables operators to select a type of pontic and to select and modify the amount and location of a ridge contact. The pontics tool also provides for selecting occlusal and proximal parameters.

The framework design tool enables operators to select and modify the location of a cutback, amount of a cutback, location of a connector, type of a connector, and size of a connector.

The output device tool allows operators to choose a type of output that will be used to represent or fabricate the designed prostheses. This can be done by selection of a fabrication method. For example, the output can be determined by identifying whether the prostheses will be manufactured by direct metal or ceramic fabrication. In any event, a suitable output type is used for the identified fabrication process or purpose. Output conducive to the creation of a wax pattern based on the digitally designed prostheses can also be selected.

A digital wax builder tool is provided to the operator for use in adding and forming wax on prepared surfaces. 3D visualization tools provided by the system (100; FIG. 1) allow the operator to visualize a virtual dental structure from different viewpoints to determine a desired profile for a model prosthesis.

The tools and functions described above can be utilized by the dentist or technician through the user interface provided by the system (100; FIG. 1). The system (100; FIG. 1) can be configured to provide a menu of the tools and functions from which the operator can select and operate desired tools. With these tools, the operator can determine, select, and modify attributes of the virtual 3D model of the dental prosthesis. The attributes can include any attribute useful for defining a model of a dental prosthesis. Examples of such attributes include but are not limited to any of the occlusal, proximal, margin, gingival, pontic, and framework attributes discussed above. An embodiment of a menu of tools for designing virtual prostheses models is listed in Table 1.

TABLE 1

3D Prostheses Design Function Menu

A. Preparation for Fabrication Procedures
    Individual Tooth Level
        (1) Removal of artifacts
        (2) Die spacer - amount and location
    Single Arch Level
        (1) Analysis and comparison of contralateral teeth
        (2) Analysis of arch occlusal plane profile
        (3) Analysis of arch width
    Whole Mouth Level
        (1) Analysis of tooth-to-tooth occlucal relationships
        (2) Analysis of centric occlusal contacts
        (3) Analysis of eccentric contacts
        (4) Analysis of anterior guidance mechanism
        (5) Analysis of orthodontic arch relationships
B. Fabrication of Restoration
    Whole Mouth Functions
        Occlusal
            (1) Select occlusal scheme for whole mouth - if not specified as part of diagnostic assessment
            (2) Determine occlusal plane level
            (3) Determine anterior/posterior occlusal plane curvature
            (4) Determine mediolateral occlusal plane curvature
            (5) Determine centric occlusal contact scheme
            (6) Determine occlusion mechanics
    Individual Tooth Functions (crowns and retainers)
        Occlusal Tool
            (1) Select occlusal scheme if not done for whole mouth
            (2) Cusp angles can be determined from intact contralateral teeth, determined functionally or exact angles specified
            (3) Verify number of cusps for molars and premolars
            (4) Verify centric and eccentric occlusal contacts
            (5) Verify occlusal table width
            (6) Verify height and width of proximal margins
            (7) Select occlusal rests if necessary for removable partial dentures
            (8) Option to select mirror image of contralateral tooth
        Proximal Tool
            (1) Select/modify curvature shape for proximals - generally smooth convex shape from occlusal table to gingival
            (2) Verify/modify height and width of proximal contact(s)
            (3) Shape proximal contours as necessary for removable partial denture clasp arms, guide planes, or major/minor connectors
            (4) Incorporate proximal box/space for precision attachment(s)
            (5) Option to select mirror image of contralateral tooth
        Gingival Tool

TABLE 1-continued

3D Prostheses Design Function Menu (1) Select/Modify type of margin
    (2) Select/modify emergence angle
    (3) Option to select mirror image of contralateral tooth
Pontics Tool
    (1) Select type of pontic
    (2) Select/modify amount and location of ridge contact
    (3) Occlusal and proximal parameters same as retainers
Framework Design Tool
    (1) Select/modify location of cutback
    (2) Select/modify amount of cutback
    (3) Select/modify location of connector
    (4) Select/modify type of connector
    (5) Select/modify size of connector
Output Device
    (1) Wax pattern
    (2) Direct metal fabrication
    (3) Direct ceramic fabrication Once the final 3D image of the final restoration is designed (e.g., the 3D digital model), the final image can be compared to the design to determine compliance or to identify any areas that should be corrected.

When the fabricated restoration is being clinically installed, the system (100; FIG. 1) can be utilized to map the restoration at step (460) of FIG. 4 as the restoration prosthesis is being seated and adjusted in the patient's (108) dentition. In particular, the restoration can be imaged relative to its adjacent teeth to identify any seating discrepancies. The imaging of restoration prostheses during the installation process and once the restoration is in place can be used to eliminate the common practice of taking radiographs to determine when restorations are properly seated. Further, 3D imaging of the final cemented restoration can serve as a legal record of treatment and be used to provide a detailed 3D baseline for future diagnosis and treatment. Thus, the 3D imaging functions provided by the system (100; FIG. 1) can be used to enhance various aspects of dental practices, especially in the context of dental restoration work.

In conclusion, the present systems and methods present dentists and technicians with chair-side dental equipment that provides dental computer-aided design (CAD) functions that can be utilized by operators to accurately diagnose and treat dental conditions based on 3D digital impressions (116; FIG. 1). With the present systems and methods, dental prostheses (e.g., implants, inlays, caps, crowns, bridges, etc.) can be interactively designed and fabricated using virtual 3D digital models. Fabrication of prostheses may be performed on-site, thereby allowing dental restoration procedures to be performed in a single visit. Further, the accuracy provided by the virtual 3D digital models improves the quality of dental care over traditional dental restoration practices. Thus, the systems and methods described above can dramatically reduce dental costs, eliminate unnecessary time waste for both dentists and patients, and create new business opportunities in dentistry.

The preceding description has been presented only to illustrate and describe the present methods and systems. It is not intended to be exhaustive or to limit the present methods and systems to any precise form disclosed. Many modifications and variations are possible in light of the above teaching.

The foregoing embodiments were chosen and described in order to illustrate principles of the methods and systems as well as some practical applications. The preceding description enables those skilled in the art to utilize the methods and systems in various embodiments and with various modifications as are suited to the particular use contemplated. It is intended that the scope of the methods and systems be defined by the following claims.

What is claimed is:

1. An interactive dental computer-aided design (CAD) system, comprising:
a three-dimensional camera configured to project a spatially varying pattern of light on a patient's dentition and image said dentition; wherein, using said spatially varying pattern of light and triangulation, said three-dimensional camera outputs a three-dimensional model of said dentition;
a graphical user interface for displaying a representation of said three-dimensional (3D) model image for viewing by an operator;
an access interface for receiving input from the operator; and
a prosthesis design module providing design tools for creating a virtual 3D model of a dental prosthesis responsive to operator input.

2. The system of claim 1, wherein said design tools include an occlusal tool configured for selecting occlusal rests for said dental prosthesis.

3. The system of claim 1, wherein said design tools include an occlusal tool configured to determine a cusp angle from contralateral teeth.

4. The system of claim 1, wherein said design tools include an occlusal tool configured to enable the operator to control an occlusal attribute of said dental prosthesis; wherein said occlusal attribute includes any of a cusp angle, a number of cusps, an occlusal contact, an occlusal table width, an occlusal plane level, an occlusal plane curvature, an occlusal contact, or an occlusal rest.

5. The system of claim 4, wherein said occlusal tool is configured to control said occlusal attribute of said dental prosthesis based on a mirror image of a contralateral tooth.

6. The system of claim 1, wherein said design tools include a proximal tool configured to enable the operator to select and modify a curvature shape for proximals in said 3D model.

7. The system of claim 6, wherein said proximal tool is configured to modify said proximal attribute based on a mirror image of a contralateral tooth.

8. The system of claim 1, wherein said design tools include a proximal tool configured to enable the operator to modify a proximal attribute of said 3d model, wherein said proximal attribute includes any of a proximal curvature shape, a proximal contact width, or a proximal contact height.

9. The system of claim 1, wherein said design tools include a gingival tool configured to enable the operator to select or modify a type of margin and an emergence angle for said virtual 3D model.

10. The system of claim 1, wherein said design tools include a pontics tool configured to enable the operator to select a type of pontic for said virtual 3D model.

11. The system of claim 10, wherein said pontics tool is configured to enable the operator to modify pontic attributes of said virtual 3D model.

12. The system of claim 1, wherein said design tools include a framework design tool configured to enable the operator to select or modify a framework attribute for said virtual 3D model.

13. The system of claim 11, wherein said framework attribute includes a location of a cutback, an amount of a cutback, a location of a connector, a type of connector, or a size of connector.

14. The system of claim 1, wherein said design tools include an output tool configured to enable the operator to select a type of fabrication for said dental prosthesis.

15. The system of claim 1, wherein said design tools include a wax tool configured to enable the operator to shape said virtual 3D model by adding or subtracting virtual wax.

16. The system of claim 1, wherein said design tools include functions for enabling the operator to view different views of said 3D image for analyzing a patient's dentition at different contextual levels, said different levels including an individual tooth level, a single arch level, and a whole mouth level.

17. The system of claim 1, wherein said graphical user interface is configured to display a menu of dental prosthesis design functions for selection by the operator.

18. The system of claim 1, further comprising a simulation module configured to simulate placement of said virtual 3D model into a digital impression of at least part of a patient's dentition.

19. The system of claim 1, further comprising an output design data module configured to generate output data representative of said virtual 3D model in a format selected by the operator.

20. The system of claim 1, further comprising an image processing module configured to provide the operator with interactive tools for preprocessing said 3D image.

21. The system of claim 1, wherein said prosthesis design module provides preparation tools configured to assist the operator with preparations for dental restoration treatment.

22. The system of claim 21, wherein said preparation tools include an axial alignment tool, a margin design tool, a tooth reduction tool, and a retention and resistance form tool.

23. The system of claim 1, wherein said camera captures both two-dimensional images and said three-dimensional model of said dentition.

24. The system of claim 23, further comprising an overlayer for registering said two-dimensional and images and said three-dimensional model of said dentition.

25. The system of claim 1, wherein said design tools comprise a measurer for extracting dentition measurements from said 3D model.

26. The system of claim 1, wherein said camera further comprises a merger tool that integrates multiple un-calibrated 3D images to form said 3D model.

27. An interactive dental computer-aided design (CAD) system, comprising:

a three-dimensional camera configured to produce a three-dimensional model of said dentition;

a graphical user interface for displaying a representation of said three-dimensional (3D) model image for viewing by an operator;

an access interface for receiving input from the operator; and a prosthesis design module providing design tools for creating a virtual 3D model of a dental prosthesis responsive to operator input 28. The system of claim 27, wherein said design tools include an occlusal tool configured for selecting occlusal rests for said dental prosthesis.

29. The system of claim 27, wherein said design tools include an occlusal tool configured to determine a cusp angle from contralateral teeth.

30. The system of claim 27, wherein said design tools include an occlusal tool configured to enable the operator to control an occlusal attribute of said dental prosthesis; wherein said occlusal attribute includes any of a cusp angle, a number of cusps, an occlusal contact, an occlusal table width, an occlusal plane level, an occlusal plane curvature, an occlusal contact, or an occlusal rest.

31. The system of claim 27, wherein said design tools include a proximal tool configured to enable the operator to select and modify a curvature shape for proximals in said 3D model.

32. The system of claim 27, wherein said design tools include a proximal tool configured to enable the operator to modify a proximal attribute of said 3d model, wherein said proximal attribute includes any of a proximal curvature shape, a proximal contact width, or a proximal contact height.

33. The system of claim 32, wherein said proximal tool is configured to modify said proximal attribute based on a mirror image of a contralateral tooth.

34. The system of claim 27, wherein said design tools include a gingival tool configured to enable the operator to select or modify a type of margin and an emergence angle for said virtual 3D model.

35. The system of claim 27, wherein said design tools include a pontics tool configured to enable the operator to select a type of pontic for said virtual 3D model.

36. The system of claim 35, wherein said pontics tool is configured to enable the operator to modify pontic attributes of said virtual 3D model.

* * * * *